US010420463B2

(12) United States Patent
Dick et al.

(10) Patent No.: US 10,420,463 B2
(45) Date of Patent: Sep. 24, 2019

(54) METHOD FOR DETERMINING THE TOPOGRAPHY OF THE CORNEA OF AN EYE

(71) Applicant: Carl Zeiss Meditec AG, Jena (DE)

(72) Inventors: Manfred Dick, Gefell (DE); Ferid Bajramovic, Jena (DE); Wei-Jun Chen, Jena (DE); Tobias Bühren, Magdala (DE); Matthias Reich, Jena (DE); Jörg Meissner, Jena (DE); Martin Kühner, Bad Klosterlausnitz (DE)

(73) Assignee: Carl Zeiss Meditec AG, Jena (DE)

( * ) Notice: Subject to any disclaimer, the term of this patent is extended or adjusted under 35 U.S.C. 154(b) by 0 days.

(21) Appl. No.: 15/745,551

(22) PCT Filed: Jul. 6, 2016

(86) PCT No.: PCT/EP2016/066041
§ 371 (c)(1),
(2) Date: Jan. 17, 2018

(87) PCT Pub. No.: WO2017/016835
PCT Pub. Date: Feb. 2, 2017

(65) Prior Publication Data
US 2018/0206718 A1 Jul. 26, 2018

(30) Foreign Application Priority Data

Jul. 24, 2015 (DE) .................. 10 2015 009 642

(51) Int. Cl.
*A61B 3/107* (2006.01)
*A61B 3/10* (2006.01)
*A61B 3/14* (2006.01)
*A61B 3/18* (2006.01)

(52) U.S. Cl.
CPC .............. *A61B 3/107* (2013.01); *A61B 3/102* (2013.01); *A61B 3/14* (2013.01); *A61B 3/18* (2013.01)

(58) Field of Classification Search
CPC ........... A61B 3/0025; A61B 3/14; A61B 3/12; A61B 3/113; A61B 3/102
USPC ........................................................ 351/246
See application file for complete search history.

(56) References Cited

U.S. PATENT DOCUMENTS 8,770,753 B2 7/2014 Hee et al.
2011/0222020 A1* 9/2011 Izatt ...................... A61B 3/102
351/205

2013/0329187 A1* 12/2013 Steinmueller .......... A61B 5/721
351/206
2014/0049753 A1* 2/2014 Bajramovic .......... A61B 3/1005
351/247
2015/0031993 A1* 1/2015 Buckland ............... A61B 3/102
600/425

FOREIGN PATENT DOCUMENTS

DE 699 06 779 T2 1/2014
DE 10 2012 019469 A1 4/2014
DE 10 2012 019474 A1 4/2014

OTHER PUBLICATIONS

PCT International Preliminary Report on Patentability and Written Opinion for International Application No. PCT/EP2016/066041, dated Feb. 8, 2018, 8 pages.
PCT International Search Report and Written Opinion for International Application No. PCT/EP2016/066041, dated Oct. 5, 2016, 10 pages.
English translation of PCT International Search Report for International Application No. PCT/EP2016/066041, dated Oct. 5, 2016, 2 pages.
DE Search Report for 10 2015 009 642.7, dated Nov. 2, 2016, 9 pages.
Ortiz, Sergio, et al.; "Corneal topography from spectral optical coherence tomography (sOCT)", Biomedical Optical Express, vol. 2, No. 12, 2011, 3232-3247.
Karnowski, Karol, et al.; "Corneal topography with high-speed swept source OCT in clinical examination", Biomediacal Optical Express, vol. 2, No. 9, 2011, 2709-2720.
Izatt, Joseph A., et al.; "Expanding the use of OCT", Optics & Photonics News, Apr. 2014, 34-41.
Oltrup, T., et al.; "Placido-Hornhauttopographie kombiniert mi optischer Biometrie—erste Egebnisse"; Klinische Monatsblaetter der Augenheilkunde 2013; 230, 519-523, published in Germany CZ—Jan. 2015; © Carl Zeiss Meditec AG, 2014.

* cited by examiner

*Primary Examiner* — Mohammed A Hasan
(74) *Attorney, Agent, or Firm* — Patterson Thuente Pedersen, P.A.

(57) ABSTRACT

A method for determining the topography of the cornea of an eye on the basis of an optical, contactless data capture. In the method for determining the topography of the cornea of an eye, which is based on a deflectometric method, the deflectometric measurements are carried out with the aid of a keratometric method by virtue of additional OCT-based scans being made at the keratometric measurement points, wherein the two measurement systems are registered to one another and both the keratometric and the OCT-based measurement values are recorded and used for mutual calibration to determine and output the topographic data. The proposed method serves to determine the topography of the cornea of an eye. It is helpful to ascertain the topography in order to be able to draw conclusions about possible pathological changes. Moreover, the exact measurement of the corneal topography is of great importance for correcting refractive errors.

21 Claims, No Drawings

METHOD FOR DETERMINING THE TOPOGRAPHY OF THE CORNEA OF AN EYE

RELATED APPLICATIONS

This application is a National Phase entry of PCT Application No. PCT/EP2016066041 filed Jul. 6, 2016 which application claims the benefit of priority to German Application No. 102015009642.7, filed Jul. 24, 2015, the entire disclosures of which are incorporated herein by reference.

FIELD OF THE INVENTION

The present invention relates to a method for determining the topography of the cornea of an eye, on the basis of an optical, contactless data capture.

BACKGROUND

The corneal topography of an eye involves a micrometer-accurate examination method of the cornea, in which some kind of a map of the surface of the cornea is created. The ophthalmologist measures the extent of the curvature of the cornea at thousands of single points. The corneal topography provides an exact image of the curvature of the cornea. Based on these results, the ophthalmologist can determine possible pathological changes. The exact measurement of the corneal topography is also of great importance for correcting refractive errors.

In view of newer applications, such as
 cataract surgery,
 IOL determination,
 contact lens adjustment, and
 refractive laser surgery,
topographic procedures face special challenges regarding accuracy and reproducibility of the measurements, which make it desirable to improve the traditional topographic procedures or develop new methods.

The currently known topographic procedures are based on specially adapted methods of deflectometry, fringe projection and triangulation. For example, it is possible to determine accurately the corneal radii up to app. +/−0.05 mm, using a keratometer or an ophthalmometer.

The term deflectometry involves the contactless capture or measurement of reflective surfaces, in which technologies from photometry or radiometry, photogrammetry, laser scanning or laser distance measurement are used.

The keratometer is an instrument for measuring the surface curvature of the cornea of an eye and for determining the corneal progression. In the process, an illuminated object is placed at a known distance and the reflection of the cornea is measured to be able to draw conclusions about the curvature of the cornea.

Two further traditional topographic procedures are based on the projection of a placido-ring system or the use of a Scheimpflug camera.

In the placido-ring-based method, a system of alternating black and light rings is projected at regular intervals on the anterior corneal surface. By evaluating the reflection of the ring system on the cornea, the anterior corneal surface can be reconstructed visually, and its curvature can be measured.

In the Scheimpflug method, on the other hand, pictures are taken with the camera from different viewing directions and these pictures are used to determine the shape of the anterior and posterior surface of the cornea.

With these two topography devices, elevation data can be collected with an accuracy of app. 1 μm.

Newer topography methods include the optical coherence tomography (OCT), which currently allows for a low resolution in the range of app. 10 μm, which can be increased in the future in the accuracy range of less μm. However, compared to traditional topography methods, these systems are very expensive.

The basic principle of the OCT method is based on white-light interferometry and compares the duration of a signal by application of an interferometer (commonly a Michelson Interferometer). For this purpose, an arm with known optical path length (=reference arm) is used as reference for the measuring arm. The interference of the signals of both arms results in a pattern from which the relative optical path length within an A scan (single low signal) can be read. In the one-dimensional screening methods, the beam is guided transversally in one or two directions, analogous to ultrasound technology, whereby it is possible to record a flat B-scan or a three-dimensional tomogram (C-scan). For example, for one A-scan comprising 100 single A-scans one second of measuring time is required.

The measurement resolution of the OCT method is determined by the so-called coherence length of the light source used which is approximately 15 μm. Because of its special aptitude for examining optically transparent media, the method is widely used in ophthalmology.

In OCT methods used in ophthalmology, two different types have been established. To determine the measuring values, in the first type, the length of the reference arm was changed, and the intensity of the interference was continually measured, without taking the range into consideration. This method is described as "time domain" method. However, in the other method, which is described as "frequency domain", the range is considered for determining the measuring values and the interference of the single spectral components is captured. Therefore, one is called a signal in the time domain, and the other a signal in the frequency domain.

In current prior art, different types of work have become known, which use OCT data for determining the topography of the cornea of an eye and compare them with conventional methods.

U.S. Pat. No. 8,770,753 B2 discloses multiple radial and circular OCT scan patterns centered on the cornea and the anterior eye segment to determine with these data, among other things, the topography and pachymetry of the cornea. For a long time the analysis of data of the cornea (anterior and posterior surface) has been examined in research on the basis of OCT methods, while still facing different challenges:

1. OCT imaging usually has an adequate axial depth resolution but a limited lateral resolution. This often results from poor image reproduction of the corneal surface.
2. The spatial positions of the cornea, in which information from the OCT scan is available depend on the design of the scan pattern. For example, it is desirable that denser scans are produced over critical areas of the cornea, and less scans are required in the more continuous regions.
3. To be able to determine an accurate topography of the cornea, repeated and accurate monitoring and control of the scanners are necessary.

4. In order to have accurate synchronization between the OCT scan data and the dynamic of eye fixation or ocular movement, an additional quick eye tracker is required.
5. Alternatively, to solve the problem under 4), an ultra-highspeed OCT scanner is necessary, which can collect the complete data record in the ms range analogous to the camera systems. Only in this case would ocular movement not play any part. Currently, such scanner systems are not available.
6. As a further alternative solution to 4), a robust and accurate motion detection could be determined from the OCT data, in order to correct the resulting topographic data according to the movements.

In [1], Sergio Ortiz et al. collect corneal topographic data by use of a spectral domain OCT (s-OCT). There, distortions based on OCT scan geometry are compensated, and the problems of ocular movement during the scanning period are discussed. The OCT topographic data collected by use of test objects and patient data are compared with placido data and Scheimpflug data of conventional corneal topography and evaluations are presented. It is assumed that OCT topography is feasible, but there are still some problems to be solved.

In [2], Karol Karnowski et al. collect and examine in a clinical study topographic data with swept source OCT. Because of the high speed of the ss-OCT method, it was already possible to collect within the time period <0.25 s a dense data network for corneal topography and compare said data with the conventional placido and Scheimpflug data for topography. The axial resolution of the ss-OCT system important for collecting elevation data of the cornea amounted to only 20 μm. Considering that in a corrective refraction of the cornea by application of LASIK, in an optical zone of 5.5 mm, centrally only approximately 10 μm tissue is removed for a dioptric correction, it would only be possible to achieve an accuracy of 2 D, which is unacceptable and demonstrates the current limitations of the prior art.

In [3], among other things, the advantages of using OCT-based topography are discussed in comparison with conventional keratometry and topography. In this context, the complete representation of the cornea by application of OCT is evaluated as being very important, especially when the cornea has been changed by refractive laser surgery. To be able to control the problem of ocular movement artefacts with comparatively slow OCT, optimized scan strategies are specified, which allow for an improved evaluation of the scan data. By means of correction procedures with regard to optical distortions of the OTC, it was possible to achieve a correlation of the topographic data of 0.1+/−0.53 D collected in comparison to the simulated keratometry from topographic data.

In [4], the combination of placido-topographic data and biometric data, which were collected by means of OCT for eye length, were discussed by T. Oltrup, et al. The aim is to open up new possibilities for determining artificial intraocular lenses (IOL). Here, the topographic data are determined in conventional manner, and, when using the IOLMaster 500, an A scan is used for length measurements of the eyes.

Prior art shows that efforts are made to use the OCT methods also for collecting topographic data of the cornea. Based on scan geometries provided for the OCT, correction procedures are required to be able to specify the real corneal topography. Through measurements on a reference object, it was possible to evaluate in principle and show the validity of the correction for a spherical shape ([2]).

Compared to conventional methods of keratometry and placido topography, which can collect a data set without distracting eye movements by means of camera chip exposure, the relatively long scan period of the OCT method has a disadvantage and requires further correction procedures.

The axial resolution of the OCT methods is limited by the spectral scanning width of the laser source. With the high-resolution OCT of approximately 50 nm, it is possible to obtain approximately 5-6 μm. With the ultra-high-resolution OCT, for example on the basis of complex fs lasers, it is possible to obtain app. 1-3 μm with approximately 1000 nm.

There is a deficiency in prior art in that it is currently not possible to provide topographic data of the cornea with currently available cost-effective OCT systems. In addition to resolution and reproducibility, the long scanning period in connection with the ocular movement is a problem that can currently only be controlled with additional eye trackers.

Combination devices having a placido-ring projection and an OCT device would require a comparatively large installation space, wherein the placido disc particularly limits the operator's view on an eye pair and results in time-consuming processes. When a large diameter is to be achieved in the topography of up to app. 16 mm all the way to the area of the sclera, the placido projector would require correspondingly larger diameters and would further complicate the handling process, or there would be a very limited implementation for the optical design.

A further disadvantage of the conventional placido topography and even keratometry involves the lack of measuring data in the central optical zone of app. 2 mm-0.8 mm diameter, because these would be used for data acquisition with the measuring camera.

Furthermore, a tear film outline during deflectometric recordings results in an internal distortion of the measuring point on the camera and complicates the process of finding the focus and reduces the measuring accuracy.

The new IOLMaster® 700 by Zeiss [5] already collects B scans for measuring the biometric axial distances in an eye and thus also a data set for surface topography of the cornea. This system, in which a visual examination of the obtained biometric data based on OCT images takes place, is characterized by better refractive results with high repeatability and clinical databank connection. In addition, the collection of OCT data is feasible with a comparatively low standard deviation of reproducibility. The following measuring accuracies can be obtained with this system:

Central corneal thickness: +/−2 μm
Anterior chamber depth: +/−11 μm
However, to this system with a comparatively slow scan rate, the above-mentioned current disadvantages can be applied.

LITERATURE

[1] Ortiz, Sergio, et al.; "Corneal topography from spectral optical coherence tomography (sOCT)", Biomedical Optical Express, vol. 2, no. 12, 2011, 3232-3247
[2] Karnowski, Karol, et al.; "Corneal topography with high-speed swept source OCT in clinical examination", Biomediacal Optical Express, vol. 2, no. 9, 2011, 2709-2720
[3] Izatt, Joseph A., et al.; "Expanding the use of OCT", Optics & Photonics News, April 2014, 34-41
[4] Oltrup, T., et al.; "Placido-Hornhauttopographie kombiniert mi optischer Biometrie—erste Egebnisse"; Klinische Monatsblaetter der Augenheilkunde 2013; 230, 519-523, published in Germany CZ-January 2015; ©Carl Zeiss Meditec AG, 2014.

SUMMARY OF THE INVENTION

The present invention includes a method for determining the topography of the cornea of an eye, which meets the growing requirements for accuracy and reproducibility of measuring data and, at the same time, allows for a quantitative evaluation of the measuring data. Furthermore, embodiments of the invention make it possible to collect data even outside of the optically relevant diameter range of the cornea of up to 8 mm.

According to example embodiments of the invention, a method for determining the topography of the cornea of an eye on the basis of a deflectometric method in that the deflectometric measurements are carried out with the aid of a keratometric method, in that additional OCT-based scans are realized at the keratometric measurement points, wherein the two measurement systems are registered to one another and both the keratometric and the OCT-based measurement values are recorded and used for mutual calibration in order to determine and output the topographic data.

The proposed method serves to determine the topography of the cornea of an eye. It is necessary to ascertain the topography in order to be able to draw conclusions about possible pathological changes. Moreover, the exact measurement of the corneal topography is of great importance for correcting refractive errors.

Subsequently, the invention is described in more detail by presentation of example embodiments.

In an example inventive method for determining the topography of the cornea of an eye based on a deflectometric method, deflectometric measurements are carried out with the aid of a keratometric method by virtue of additional OCT-based scans being realized at the keratometric measurement points, wherein the two measurement systems are registered to one another and both the keratometric and the OCT-based measurement values are recorded and used for mutual calibration in order to determine and output the topographic data.

In this context, deflectometric methods involve methods, which use keratometer and placido-ring-based topographic systems.

According to an example embodiment of the invention, at least one, for example multiple keratometric measurements are made during the OCT-based scans, wherein each keratometric measurement is carried out at the time of the OCT-based scan by use of a keratometric measuring point, wherein both measuring systems are registered to one another.

In particular, recorded characteristics of an eye can be detected in the OCT-based scans and the keratometric measuring values, and can be used for mutual registration.

According to the invention, for mutual calibration it is required that at least one keratometric measuring point of at least one OCT-based scan is recorded.

However, for example multiple, and in another example all keratometric measuring points are recorded by OCT-based scans, which makes the calibration more reliable and more accurate.

According to an example embodiment OCT-based scans run centered to the apex of the cornea, thus capturing for example two or more keratometric measuring points. However, it is also possible to provide additional scan, which are offset from the OCT-based scans. Besides linear scans, it is also possible to use circular scans.

The proposed solution is based on a combination of two different measuring methods. To this end, the topographic data obtained by keratometry should be based especially on collimated illumination of the cornea and/or an image of the reflection images obtained by use of telecentric optics. In particular, exposure times in the ms range are used for keratometric measurements. These very short exposure times have the advantage that the keratometric measurements do not show any movement artefacts.

According to an example embodiment of the inventive method, 6 measuring points, or another example embodiment 18 measuring points, in a further example embodiment more than 18 measuring points are used for the keratometric measurement.

According to another example embodiment of the inventive method, the patterns of the OCT-based scans are adapted to the individual needs and local conditions.

The topography and keratometry involve measuring rings and measuring points, which are hardware-technically preset in the position. Modern topographic systems allow for measuring the corneal surface with a close-knit network of measuring points, by which non-pathological and may pathological corneas can be well depicted as long as the surface does not deviate too far from an ideal spherical shape. However, in extreme pathologies, for example, scars, the deviations are too great. As a result, in the resulting reflection images, the illumination pattern can at some places no longer be clearly associated. In these regions, it is therefore not possible to determine the surface with conventional deflectometric measuring methods.

By contrast, OCT systems are very flexible in programming scan geometries. For example, in addition to scan patterns for global measurements of the entire corneal and partially scleral ocular surface, it is also possible to generate higher resolution scan patterns in order to obtain increased comparability, and thus calibration capability, of measuring data in the surroundings of keratometric measuring points.

The fact that in an OCT measurement the corneal surface must be scanned point-by-point results in comparatively long measuring periods for complete characterization. This is of disadvantage for the patient's comfort and effect on movement. Therefore, according to example embodiments fo the invention the scanning of the cornea by application of OCT is not performed evenly but is adapted to the coverage areas of a deflectometric measurement. Areas in which the deflectometric measurement does not provide evaluable data are scanned with higher spatial density or with more repetitions. For example, these areas involve the center around the vertex, peripheral areas and places with extreme pathological changes.

According to example embodiments of the invention, OCT-based scans take place synchronously to a keratometric measurement in that in each scan pattern in which at least one OCT-based scan runs through one of the keratometric measuring points a keratometric measurement takes place.

As a result, the keratometric and OCT-based measurements provide measuring values, which are comparable with regard to time and place and which are used for calibrating both measuring modalities.

In a sequence of recording, for example, 6 consecutive keratometric measurements, temporal synchronization is provided in that in each keratometric measurement, simultaneously at one respective measuring point on the cornea, the OCT scan takes place at this point. This ensures that with regard to time and place comparable measuring data are used for the calibration of both measuring modalities. According to the invention, the measuring data thus collected serve to reconstruct also the continuous course of ocular movement in comparison to the, for example, 6 correlated measuring points and the continuously collected OCT data. For this purpose, support points regarding eye position are provided from the keratometric image and the OCT image, for example, the limbus, the iris or the anterior chamber geometry.

The deciding factor here is that the OCT data obtained with the various OCT methods are calibrated by the B-scan or other scan procedures with each measurement based on keratometric data. In addition to scanning systems, it is also possible to use OCT methods with a linear detector or surface detector for OCT-based data capture. This enables the available commercial OCT technology to collect highly reliable and accurate topographic data of the cornea.

According to a third example embodiment of the inventive method, the measuring values of the keratometric and OCT-based measurements are used to reconstruct the continuous course of ocular movement by detecting and comparing support points regarding eye position from the keratometric and OCT-based measuring image.

A correction of ocular movement can occur by taking a series of pictures simultaneously to scanning from which the position of the corneal-vertex can be determined at different points in time, so that for each measuring point of the OCT-based measurement its relation to the optical device axis can be detected.

In lateral ocular movements, only the center of the reflection pattern, which comprises, for example, 6 points, changes in a keratometric measurement, but not the position of the individual points to each other. Therefore, it is possible in a simple way to determine the ocular movement by use of a series of consecutive keratometric images.

Therefore, during the process of scanning the cornea with the OCT measuring beam, simultaneously a series of keratometric images is taken. Because of the well-known temporal beam deflection course of the OCT measurement, the scanning place for each measuring point (A-scan) in relation to the optical device axis is known. Moreover, the position of the cornea-vertex can be determined at different points in time from the keratometric images. It is therefore easy to detect and even correct ocular movements when evaluating OCT measuring data.

As a result, it is not required to perform a type of eye tracking, which is known from prior art. Because of the synchronization process, the same cornea is simultaneously measured with both imaging modalities of deflectometry and OCT. Therefore, it can be ensured that the determined data are consistent, and it can be assumed that the topographic data matches completely.

According to a further advantageous embodiment of the inventive method, the gradients of the elevation profile of the keratometric measuring points are extracted from the keratometric and OCT-based measuring values and used as a quality standard in that a warning message for deviations above a specified limit value is issued and the measurement is rejected.

In the keratometric measurement with the IOLMaster, the cornea is illuminated, for example, with 6 parallel light beams from different room directions. Via telecentric optics, the resulting reflections are displayed and recorded on a camera. The centers of the 6 illuminated points in the image indicate the places of the cornea on which the gradients of the corneal elevation profile assume specific values, which are defined by their relationship to the optical measuring axis of the IOLMaster and given by the direction of incidence of the light beam.

While the gradient determined from an OCT-based scan indicates the incline of the surface along the scan direction, the gradient from the respective keratometric measuring point corresponds to the maximum inclination in this point.

This means that the gradients of the elevation profile can be used only as a quality standard for toric surfaces, if in the case of radial OCT-based scans, for example, the angle between scan direction and the gradients of the elevation profile extracted from the keratometric measuring values are taken into consideration.

This can be done in an easy way by adapting the scan patterns to the keratometric measurement by always scanning along the maximum incline.

At the keratometer measuring places, gradients of the elevation profile can also be extracted from the topographic data of the OCT measurement. They must match with regard to the amount, as well as with regard to direction.

Therefore, both measuring modes can be used as a quality standard for the measurements in that a warning message is issued to the operator for deviations above a specified limit value and the measurement is rejected.

In the process, a defined overlap between zones of the OCT and deflectometric measurement is maintained in order to ensure a better connection of the measuring data.

To ensure the usability of the collected data, it is provided that after the data has been collected a quality check for fixation is introduced, which examines in the OCT scan associated with the retina whether the foveal pit was hit by the fixation and especially whether the biometric data can be declared valid.

A further advantageous example embodiment of the inventive method provides that the OCT-based measuring values are adapted to the keratometric measuring values by searching in the OCT-based measurements those measuring points in which the gradients correspond to those of the keratometric measuring values at the measuring points and the determined OCT-based measuring points are transferred to the measuring points of the keratometric measurement.

It is assumed that the deviations basically occur through ocular movement during the OCT measurement. In the OCT elevation data those places are searched at which the gradients correspond those of the keratometric measurement at the 6 points. Then, a transformation of OCT data takes place in such a way that the determined OCT places are transferred to the places of the keratometric measurement, thus producing consistency.

According to a last example embodiment of the inventive method, the entire anterior eye surface is recorded by the OCT-based scans.

On the one hand, this has the advantage that measuring data of up to app. 16 mm diameter can be collected beyond the optically relevant diameter range of the cornea (app. 8 mm). At the same time, it is possible to represent OCT scans in the form of a dense network not only the entire corneal surface but to expand the scans, for example, beyond the limbus to the sclera. The process of capturing the data for scleral curvature allows for a more precise contact lens adaptation.

Furthermore, the OCT scans also provide data of the posterior corneal geometry, and thus pachymetry, which become increasingly important for modern methods of biometrics of an eye.

On the other hand, OCT-based scans also provide data on the innermost optical zone of an eye of <1.5 mm, which must be excluded in the methods of deflectometry because of the detection of reflection images with a central camera. However, these very real data are most important for the vision with a day pupil and, according to the invention, now get a direct real relation to measuring data.

The inventive solution provides a method for determining the topography of the cornea of an eye, which is based on an optical, contactless data capture and which meets the growing requirements on accuracy and reproducibility of measuring data.

The proposed method makes it possible to collect measuring data of up to approximately 16 mm diameter, beyond the optically relevant diameter range of the cornea of approximately 8 mm, as well as of the innermost optical zone of an eye of <1.5 mm.

The fact that two basically different methods are combined ensures a very high protection of measuring data, which could never be obtained with a single method.

According to the invention, the method for determining the topography of the cornea of an eye on the basis of an keratometric approach is supplemented by an optical method of coherence tomography (OCT).

This has the advantage that the OCT scans have no basic limitation, because only the scanning angle range of the OCT scanner determines the diameter, having comparatively little influence on the device dimension. According to the invention, this allows for a calibrated expansion of the measuring range of the topography up to a diameter of approximately 16 mm.

The invention claimed is:

1. A method for determining topography of a cornea of an eye on a basis of a deflectometric method, comprising:
   carrying out deflectometric measurements with aid of a keratometric method that includes making keratometric measurements, wherein additional OCT-based scans are performed at keratometric measurement points;
   registering a keratometric measurement system and OCT-based measurement system to one another;
   recording both keratometric measurement values and OCT-based measurement values; and
   using the keratometric measurement values and the OCT-based measurement values for mutual calibration to determine and output the topographic data.

2. The method according to claim 1, further comprising making at least one keratometric measurement during the OCT-based scans.

3. The method according to claim 2, further comprising making multiple keratometric measurement during the OCT-based scans.

4. The method according to claim 3, further comprising performing the OCT-based scans synchronously to the keratometric measurements in that in each scan pattern in which at least one OCT-based scan runs through one of the keratometric measuring points a keratometric measurement takes place.

5. The method according to claim 2, further comprising carrying out each keratometric measurement at a time of the OCT-based scan by use of a keratometric measuring point.

6. The method according to claim 1, further comprising carrying out the keratometric measurement in a telecentric manner, wherein the measuring points are made via collimated illumination.

7. The method according to claim 1, further comprising carrying out keratometric measurements with exposure times in a ms range.

8. The method according to claim 7, further comprising using six measuring points, for the keratometric measurements.

9. The method according to claim 7, further comprising using eighteen measuring points, for the keratometric measurements.

10. The method according to claim 7, further comprising using more than eighteen measuring points for the keratometric measurements.

11. The method according to claim 1, further comprising adapting patterns of the OCT-based scans to individual needs and local conditions.

12. The method according to claims 1, further comprising performing the OCT-based scans synchronously to keratometric measurements in that in each scan pattern in which at least one OCT-based scan runs through one of the keratometric measuring points at which keratometric measurement takes place.

13. The method according to claim 1, further comprising making the keratometric measurements and the OCT measurements to supply measuring data that is compared with regard to time and place and used for calibration of both measuring modalities.

14. The method according to claim 1, further comprising using the measuring values of the keratometric and OCT-based measurements to reconstruct a continuous course of ocular movement by detecting and comparing support points regarding eye position from a keratometric and an OCT-based measuring image.

15. The method according to claim 1, further comprising extracting gradients of an elevation profile of the keratometric measuring points from the keratometric and OCT-based measuring values and using the gradients of the elevation profile as a quality standard; and issuing a warning message for deviations above a specified limit value and rejecting each measurement that deviates above the specified limit value.

16. The method according to claim 1, further comprising adapting the OCT-based measuring values to the keratometric measuring values by searching in the OCT-based measurements those measuring points in which gradients correspond to those of the keratometric measuring values at the measuring points and transferring the determined OCT-based measuring points to the measuring points of the keratometric measurement.

17. The method according to claim 1, further comprising correcting the OCT-based measuring values with regard to ocular movements occurring during a scanning process by capturing a series of images simultaneously to scanning from which the position of the corneal-vertex is determined at different points in time, so that for each measuring point of the OCT-based measurement a relation of the measuring point to the optical device axis can be detected.

18. The method according to claim 1, further comprising recording an entire anterior eye surface by the OCT-based scans.

19. The method according to claim 1, further comprising detecting special characteristics of an eye in the OCT-based scans and using the keratometric measuring values for mutual registration.

20. The method according to claim 1, further comprising, using in addition to scanning systems, OCT methods with a linear detector or surface detector for OCT-based data capture.

21. A method for determining topography of a cornea of an eye on a basis of a deflectometric method, comprising:
   carrying out deflectometric measurements with aid of a placido-ring-based topographic system that includes making topographic measurements, wherein additional OCT-based scans are performed at topographic measurement points;
   registering the placido-ring-based topographic system and OCT-based measurement system to one another;

recording both topographic measurement values and OCT-based measurement values; and using the topographic measurement values and the OCT-based measurement values for mutual calibration to determine and output topographic data.

* * * * *